(12) United States Patent
Kellerman

(10) Patent No.: US 6,205,685 B1
(45) Date of Patent: *Mar. 27, 2001

(54) ADJUSTABLE ORTHOTIC

(75) Inventor: David Kellerman, Santa Barbara, CA (US)

(73) Assignee: Kellerman Company LLC, Beverly Hills, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/118,401

(22) Filed: Jul. 17, 1998

Related U.S. Application Data

(63) Continuation-in-part of application No. 08/157,709, filed on Nov. 24, 1993, now Pat. No. 5,799,414, which is a continuation-in-part of application No. 07/957,984, filed on Oct. 26, 1992, now abandoned, which is a continuation-in-part of application No. 07/690,661, filed on Apr. 24, 1991, now Pat. No. 5,154,682, which is a continuation-in-part of application No. 07/407,145, filed on Sep. 14, 1989, now abandoned.

(30) Foreign Application Priority Data

| Oct. 12, 1992 | (JP) | .................................................... 4-273197 |
| Oct. 13, 1992 | (AU) | ................................................... 26384/92 |
| Oct. 13, 1992 | (CA) | ..................................................... 2080416 |
| Oct. 13, 1992 | (EP) | ..................................................... 92309319 |
| Oct. 13, 1992 | (IL) | ........................................................ 103451 |

(51) Int. Cl.$^7$ .................................................. A43B 23/00
(52) U.S. Cl. .................................................. 36/44; 36/160
(58) Field of Search ................................ 36/174, 160, 159, 36/155, 43, 44, 71

(56) References Cited

U.S. PATENT DOCUMENTS

| 2,221,202 | * | 11/1940 | Ratcliff ........................................ 36/43 |
| 2,421,088 | * | 5/1947 | Sims ........................................... 36/174 |
| 2,909,854 | * | 10/1959 | Edelstein .................................... 36/43 |
| 3,084,695 | * | 4/1963 | O'Donnell .................................. 36/174 |
| 4,316,333 | * | 2/1982 | Rothschild ............................. 36/91 X |
| 4,633,877 | * | 1/1987 | Pendergast ............................ 36/44 X |
| 4,756,096 | * | 7/1988 | Meyer ........................................ 36/44 |
| 4,813,157 | * | 3/1989 | Boisvert et al. ......................... 36/44 |
| 4,841,648 | * | 6/1989 | Shaffer et al. ........................... 36/43 |
| 5,014,706 | * | 5/1991 | Philipp ................................. 36/43 X |
| 5,138,774 | * | 8/1992 | Sarkozi ............................. 36/160 X |
| 5,154,682 | * | 10/1992 | Kellerman ................................ 36/44 |
| 5,799,414 | * | 9/1998 | Kellerman ................................ 36/44 |

* cited by examiner

Primary Examiner—Ted Kavanaugh
(74) Attorney, Agent, or Firm—Lewis B. Sternfels

(57) ABSTRACT

A shoe insert that can be customized by the user to control pronation of the foot and to relieve or reduce stress at painful areas of the foot comprising a sheet of a natural material such as leather or a synthetic resin such as high density polyethylene capable of being deformed to the shape of the foot by the weight of the user. The sheet includes fastening hook or loop material on at least one surface whereby detachable cushioning elements can be attached to the film. The fastening material attached to the sheet is preferably a layer of loop cloth that continuously covers one or both surfaces of the sheet. The cushioning pads also contain a sheet of loop or hook material on one or both surfaces. When the insert with attached, spaced pads is placed in a shoe, the sheet deforms around and between the compressible pads due to the weight of the user and retains the shape when the weight is removed.

6 Claims, 4 Drawing Sheets

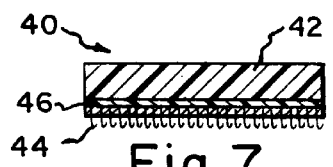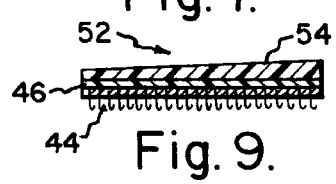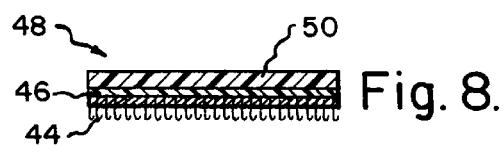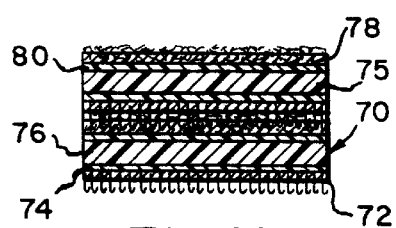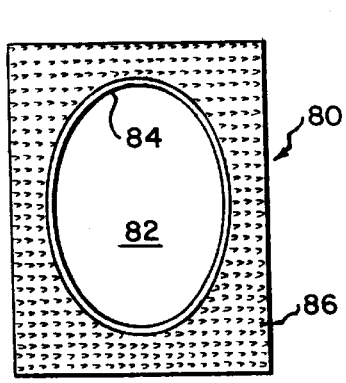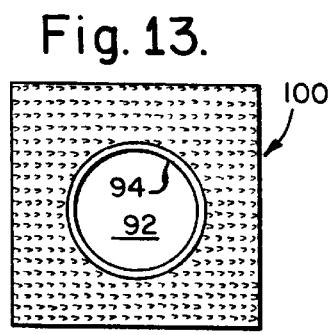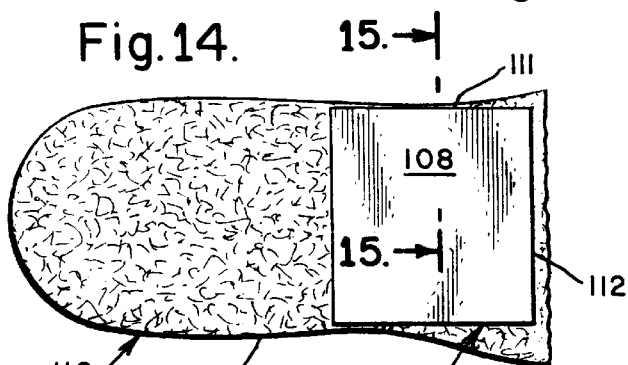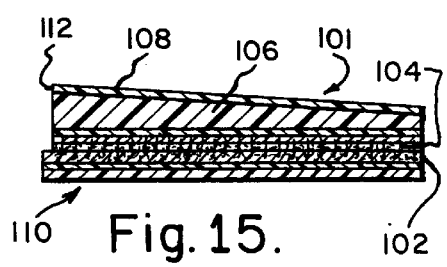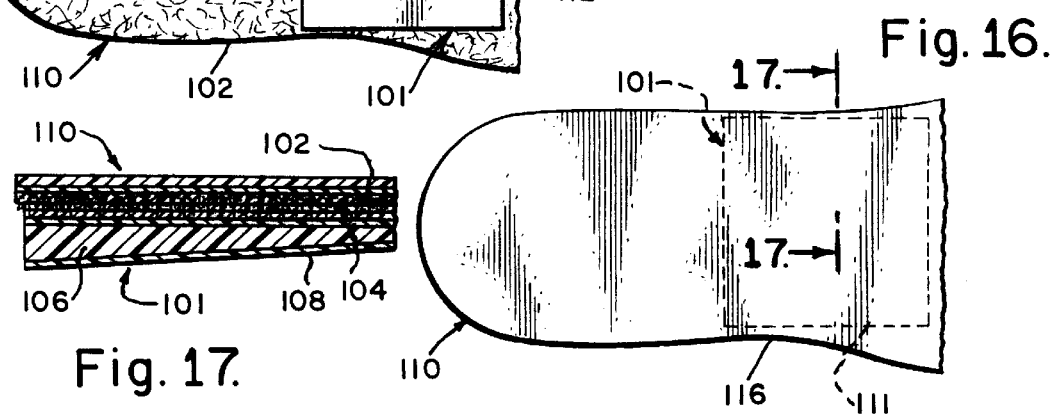

ADJUSTABLE ORTHOTIC

CROSS-REFERENCE TO RELATED APPLICATION

This application is a Continuation In Part of a pending application Ser. No. 08/157,709, filed Nov. 24, 1993, now U.S. Pat. No. 5,799,414, which is a Continuation in Part of application Ser. No. 07/957,984, filed Oct. 26, 1992, now abandoned, which is a Continuation In Part of application Ser. No. 07/690,661, filed Apr. 24, 1991, now issued on Oct. 13, 1992, as U.S. Pat. No. 5,154,682, which is a Continuation In Part of application Ser. No. 07/407,145, filed Sep. 14, 1989, now abandoned.

TECHNICAL FIELD

The present invention relates to insoles for shoes and, more particularly, this invention relates to an adjustable orthotic by which the eversion and abduction of the tarsal and metatarsal joints can be controlled by the user.

BACKGROUND OF THE INVENTION

It has been recognized that many of the minor and major traumatic conditions of the foot, leg and knee can be caused by the misalignment of the joints in the foot. These conditions can be hereditary such as the presence of a longer or shorter leg, can be acquired through traumatic injury or can be caused by repetitive stress or strain on the joints experienced during industrial or athletic activity.

Misalignment of the foot can cause minor trauma such as inflammation, blisters, rashes, calluses, corns, ingrown toe nails or more aggravated conditions such as bunions or bone spurs, typically in the heel area. Over-the-counter insoles are available to relieve minor discomfort. However, they are available in fixed sizes and thicknesses. It is possible to reduce discomfort and promote healing of inflamed areas by custom-cutting thick cushioning products such as Moleskin® into pads which can be locally adhered to the traumatic area or adjacent to the traumatic area. Pads and insoles only treat the symptoms of the misalignment and simply reduce irritation and attempt to prevent further trauma by reducing pressure, rubbing, or abrasion on the sensitive area of the foot. Sometimes surgery is utilized to remove the calluses, corns or bunions.

A more scientific approach has been to develop customized biomechanical devices that are intended to correct the misalignment of the joints. These devices, known as orthotics, are prescribed by medical specialists such as orthopedic doctors, podiatrists or doctors specializing in sports medicine. After extensive physical measurements of the patient, a plaster impression of the foot is taken. The orthotic is manufactured from the impression to specifications provided by the doctor as to the degree of pronation correction required. A soft layer of foam can be applied to the top or bottom surface of the orthotic to provide comfort and to prevent the orthotic from sliding when in a shoe.

Orthotics are very expensive, on the order of several hundred dollars a pair. Since they are so expensive, they are usually designed to provide the final correction. The degree of correction can be so severe that the orthotic causes such pain and discomfort to the patient, that it discourages usage of the orthotic and eventually it is no longer used. It is not possible to adjust the fit of the hard plastic orthotic.

STATEMENT OF THE PRIOR ART

Boisvert, et al. (U.S. Pat. No. 4,813,157) discloses a shoe insert in which the thickness of the arch region of a shoe insert can be changed by peeling off superimposed films of padding material. This product is not found on the market. This is probably because the films are adhesively secured and residual adhesive can transfer to socks and/or collect on the surface of the permanent insole. The thickness adjustment is limited to one area of the insole.

Greenwalt (U.S. Pat. No. 4,694,590) discloses an arch support unit containing preformed resilient elements located in the arch area. The support is fastened to the shoe by hook and loop fastener elements located in the heel portion of the support and adhered to the support and to the insole of the shoe. The heel cushion disclosed by Scheuerman (U.S. Pat. No. 4,928,404) contains a soft insert of silicone rubber opposite the location of a heel spur in the patients heel.

Andrews (U.S. Pat. No. 4,793,078) discloses a molded, resilient foam shoe insert having depressions 18 in the heel and in the arch support region. The depressions can be filled with adhesively secured, resilient plastic inserts 19 or may be left empty as dictated by the comfort of the wearer.

Engle (U.S. Pat. No. 4,930,232) discloses a multilayer laminated permanently adhered shoe insole formed of materials of different shore hardness.

Kristan (U.S. Pat. No. 2,928,193) discloses a composite leather-cork shoe lining filled with resilient pads of sponge or with foam rubber glued to the lining. Bittner (U.S. Pat. No. 3,143,812) discloses a thermoplastic insole that can be sized to shape by tearing off portions of the sole along heat sealed seams.

The prior insoles were mainly designed to alleviate pain and discomfort. Most of these products were formed of soft resilient materials having no memory or very hard, rigid materials that must be preformed to a desired shape. Adjustable thickness is provided only in set locations and usually by removing pads to form cushions opposite painful areas of the foot.

An insole having provision for placement of pads of varying thickness anywhere along the bottom surface of an insole is disclosed and claimed in application Ser. No. 07/690,661, filed Apr. 24, 1991, the disclosure of which is expressly incorporated herein by reference. The insole is formed of a deformable plastic with memory. The bottom surface contains longitudinal strips of loop or hook material along the bottom surface of the insole. The surface may also contain an index scale for locating the correct place to position a pad.

STATEMENT OF THE INVENTION

The present invention provides a further improvement in the design of an insole that allows it to perform as an orthotic. The insole can be modified by the user to contain elevated and/or relieved areas anywhere on the insole to form an orthotic-like device. By trial and error placement of pads of varying thickness on the bottom surface, letting comfort or discomfort be the guide, the user can create a customized therapeutic device capable of relieving pain and stress and capable of biomechanically correcting or alleviating misaligned conditions in the patient's foot. More expert alignment can be provided by a doctor of medicine trained in correcting misalignment of the feet.

The orthotic of the invention provides infinite adjustability in the location and thickness of the orthotic at any location. The orthotic can be adjusted and shaped at a doctor's clinic. The custom-shaped orthotic can be the permanently prescribed orthotic or can be a temporary device until a permanent orthotic is fabricated. The custom-configured orthotic can be shaped to provide only a fraction of the correction initially and the pads can be increased or decreased in thickness and/or location to provide gradual and more comfortable correction. The patient can be provided with a supply of pads of varying thickness and be allowed to change the pads under supervision of the clinic without the expense and inconvenience of numerous visits to the physician.

The insole of the invention is designed to permit the pads to be secured to the top or bottom surface. Since feet are symmetrical this allows the same insole to be used on the right or left foot permitting sale of single insoles. The tooling and manufacturing costs are significantly reduced.

The invention also includes specially shaped inclined ramps which when appropriately located provide pronation correction. The invention also provides pads with all edges smoothed to provide comfort to the user. The invention also relates to use of improved materials and manufacturing processes to form the insole.

These and other features and many attendant advantages of the invention will become apparent as the invention becomes better understood by reference to the following detailed description when considered in conjunction with the accompanying drawings.

BRIEF DESCRIPTION OF THE DRAWINGS

FIG. 7 is a view in section of a thick pad for attachment to the shoe insert of the invention;

FIG. 8 is a view in section of a thin pad for attachment to the shoe inserts of the invention;

FIG. 9 is a view in section of an inclined pad;

FIG. 10 is a view in section of a pad having rounded outer edges;

FIG. 11 is a view in section of a stacked assembly at a plurality of ads;

FIG. 12 is a view in section of a pad having a cavity disposed in the metatarsal region;

FIG. 13 is a view in section of a pad having a cavity over the heel region;

FIG. 14 is a view in elevation showing the assembly of an inclined pad to the top surface a shoe insert;

FIG. 15 is a view in section taken along line 15—15 of FIG. 14;

FIG. 16 is a view in section showing an inclined pad in dotted lines attached to the opposite side of a shoe insert;

FIG. 17 is a view in section taken along line 17—17 of FIG. 16;

DETAILED DESCRIPTION OF THE INVENTION

Figure 1:
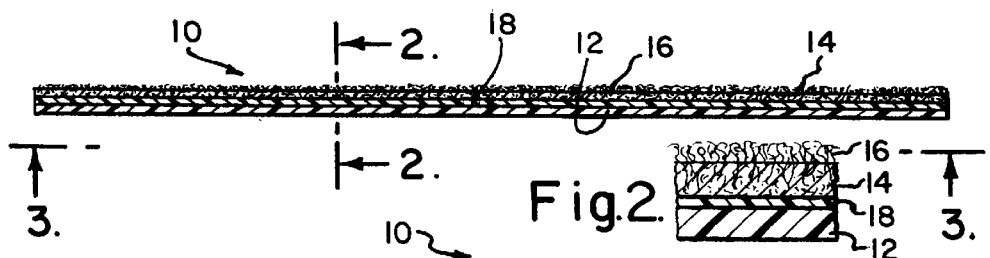
FIG. 1 is a view in section of an adjustable shoe insert according to the invention.
Figure 2:
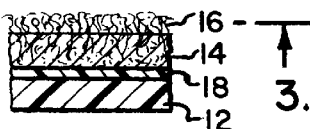
FIG. 2 is a view in section taken along line 2—2 of FIG. 1.
Figure 3:
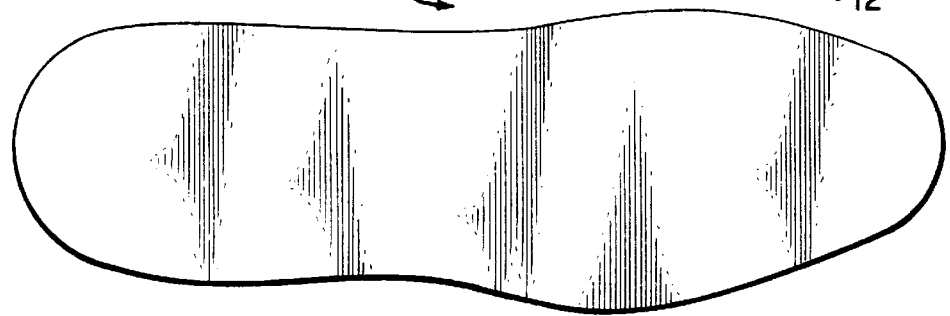
FIG. 3 is a view in elevation taken in the direction of lines 3—3 of FIG. 1.

Referring now to FIGS. 1–3, the shoe insert 10 of the invention is a multilayer laminate in the shape of a shoe insole. The insert 10 comprises a base layer 12 and an outer pad attaching layer 14. The base layer 12 preferably contains a sheet of cloth having loops 16 to which compressible pads having a layer of hooks can attach. The attachment layer can form the upper surface of an insole or be disposed toward the bottom surface. The layer 14 is attached to the base 12 by bonding, suitably by means of a layer 18 of adhesive. Optionally a cushioning layer 20 of closed cell foam such as Poron or other elastomeric material can also be present.

The base preferably contains a continuous, non-compressible sheet of a flexible but deformable sheet of natural material or synthetic organic resin with memory such as a 10–100 mil thick sheet of thermoplastic resin such as a vinyl resin, polyethylene or polypropylene, preferably a high density polyethylene (HDPE), preferably from 10 to 30 mil. A non-compressible sheet of flexible but deformable material such as leather can also be utilized. Under the force of the weight of the user, cushion pads placed on the lower surface of the sheet will compress and the sheet of resin will deform and mold to the shape of the foot forming gradual ramps as the sheet deforms around and between pads. The sheet will also deform into cavities formed in pads such as shown in FIGS. 12 and 13 and into cavities formed between adjacent pads. The base sheet preferably is not foamed and does not contain any open or closed cells. Organic materials such as HDPE and leather also present a low friction, seamless surface when used as the upper surface of the insert. The smooth surface reduces irritation and can result in reduction of inflammation and swelling.

The loop fabric is preferably formed of a synthetic resin such as a polyamide material (e.g., Nylon®) and contains a loop surface adapted for releasable engagement by hooks. The loop fabric is commercially available laminated to foam backing layers such as polyester or polyurethane foam cores in various thicknesses. These materials have been used in industrial applications such as display panels office partitions, bulletin boards, etc. These loop fabrics are washable with water and detergent or can be cleaned with organic solvent to remove common stains. An example of a commercial loop cloth is Veltex Bright materials.

The Veltex nylon cloth materials have a thin, low profile and will not fray. They are available in many colors and can be attached by pressure sensitive adhesives, tapes, ultrasonic, or thermal bonding.

Figure 4:
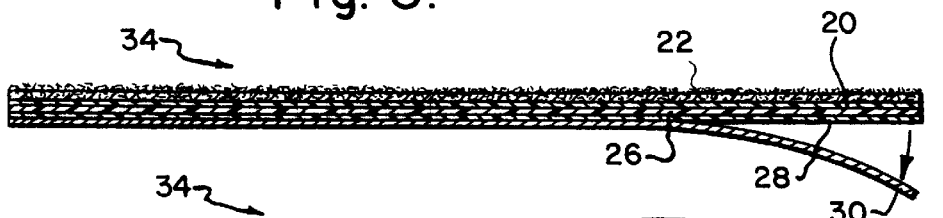
FIG. 4 is a view in section of another embodiment of an adjustable shoe insert.
Figure 5:
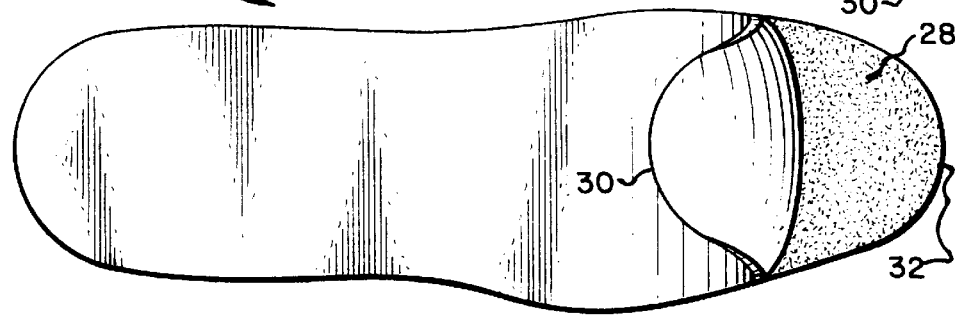
FIG. 5 is a view in elevation of the shoe insert of FIG. 4 shown with the lowermost layer being peeled away.
Figure 6:
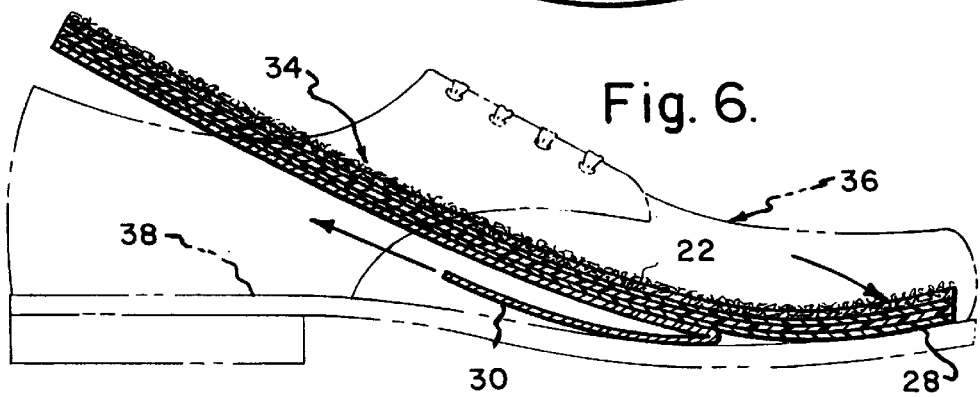
FIG. 6 is a view in section of the shoe insert of FIG. 4 illustrated being inserted into a shoe.

Referring now to FIGS. 4–6, a cloth layer 22 and foam layer 20 are adhered to the deformable base 26. The lower surface of the base contains a layer 28 of adhesive covered by a protective sheet 30. As the sheet 30 is peeled from the top edge 32 of the shoe insert 34, the adhesive layer 28 is exposed. When the insert is placed in a shoe 36, the adhesive layer 28 will adhere to the surface 38 of the insole. The protective sheet 30 is then removed. The cloth layer 22 is exposed for adherence of pads containing cooperatively engaging hook material.

The preferred hook materials used with the pads are also preferably formed of a thin, low profile, non-frayable material. The hooks can form bonds with the loop material of from 20 to 100 pounds per inch, usually around 60–80 pounds per inch. Preferred materials have good elongation properties. Again the preferred hook materials are formed of Nylon. They can be precoated with adhesive. A suitable commercial material is ULTRA-MATE hook materials.

Various pad configurations are illustrated in FIGS. 7–13. Each pad contains a cushioning layer formed of a resilient material, suitably a closed cell foam such as PORON. The pads can vary in thickness but generally are from about ⅛ inch to about ½ inch in thickness. The hook material is bonded to the cushioning layer by adhesive, thermal or ultrasonic bonding or by adhesive tape.

Referring now to FIG. 7, a thick pad element 40 has a cushioning layer 42 attached to a layer 44 of hook material by a film 46 of adhesive. The thin pad element 48 shown in FIG. 8 contains a thinner layer 50 of cushioning material. The pronation pad 52 illustrated in FIG. 9 includes an inclined cushioning layer 54. The pad 56 illustrated in FIG. 10 has rounded edges 58, 60 and can include a top layer 62 of hook or loop material so that pads can be stacked as shown in FIG. 11.

In FIG. 11 the lowermost pad 70 has a bottom hook layer 72 attached by adhesive film 74 to a cushioning layer 76 and an upper loop cloth layer 78 attached to the cushioning layer 75 by an adhesive film 80.

Figure 18:
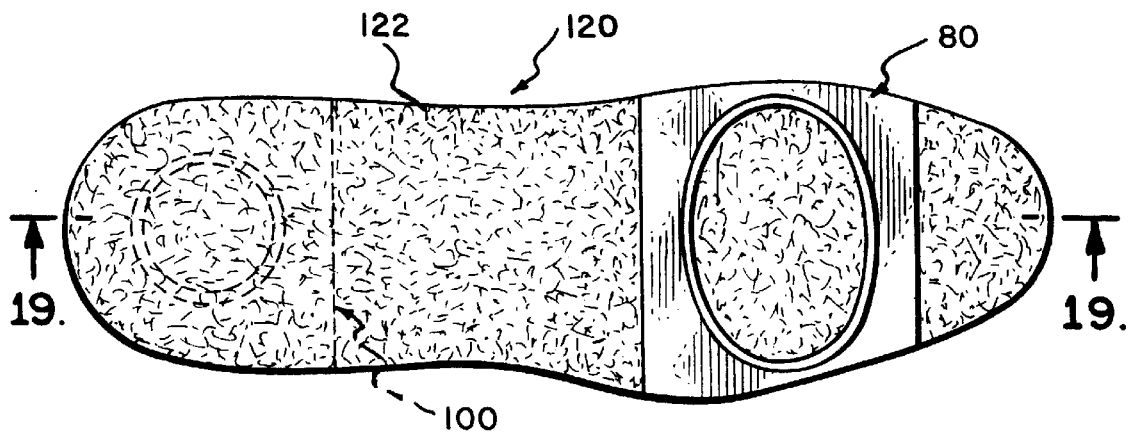
FIG. 18 is a view in elevation showing attachment of pads to the metatarsal and heel regions of a double-sided shoe insert.
Figure 19:
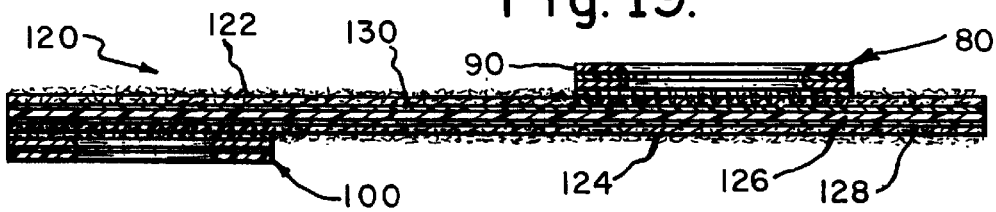
FIG. 19 is view in section taken along line 19—19 of FIG. 18.

FIGS. 12 and 13 illustrate pads with apertures which can relieve pressure when placed under sensitive areas of a foot. The larger pad 80 shown in FIG. 12 has a large oval aperture 82 cut out of the middle of the pad. The edge 84 of the cut-out is preferably smoothed or chamfered to provide comfort to the user as his foot enters the aperture 82. The attachment surface is formed of detachable material such as hook cloth 86 or loop cloth, not shown. The pad 80 can contain an internal layer 86 of cushioning material and an outer layer 90 which can be a smooth cloth such as loop cloth as shown in FIGS. 18 and 19.

The smaller pad 100 shown in FIG. 13 has a circular opening 92, otherwise the construction is identical to that of pad 80. The pad 100 is intended to be placed over inflammations on or in the heel of the user such as a heel spur. Again the edge 94 is chamfered for comfort. The pad can be cut in half and trimmed by the user to form a smaller opening. The two halves are reassembled by placing the openings adjacent each other with the hooks engaging the loops present on the surface of a shoe insert.

The pads can be attached to the top surface or bottom surface of the shoe insert. Referring now to FIGS. 14–17, inclined or ramp pad 101 is attached to the loop cloth surface 102 of a shoe insert 110. The pad 101 has a bottom hook cloth layer 104, and inclined shaped cushioning layer 106 and an upper smooth layer 108 such as loop cloth. In FIGS. 14 and 15, the shoe insert 102 is disposed with the loop cloth surface 104 facing upwardly. The pad 101 is attached across the arch and metatarsal area with the thicker edge 112 disposed along the outer edge 111 of the foot. This lift will pronate the foot inwardly to correct bow leg conditions.

The loop surface 102 of the shoe insert 110 is disposed downwardly in FIGS. 16 and 17. The hook layer 104 of the pad is attached to the loop cloth 102 with the thicker edge 111 disposed among the inner side edge 116 of the shoe insert along the arch-metatarsal region of the foot. This assembly will pronate the foot outwardly to correct a fallen arch or knock-knee condition.

Rather than inverting the shoe insert base, the base 120 as shown in FIGS. 18 and 19 can have a loop cloth layer 122, 124 on both the top and bottom surfaces. The cloth layers 122, 124 are adhered to a deformable film 126 of HDPE or other resin by adhesive layers 128, 130. Cushioning layers, not shown, may be present beneath the cloth layers.

A metatarsal pad 80 can be attached to the top loop cloth layer 122 and a heel pad 100 can be attached to the bottom loop cloth layer 124, as shown.

Figure 20:
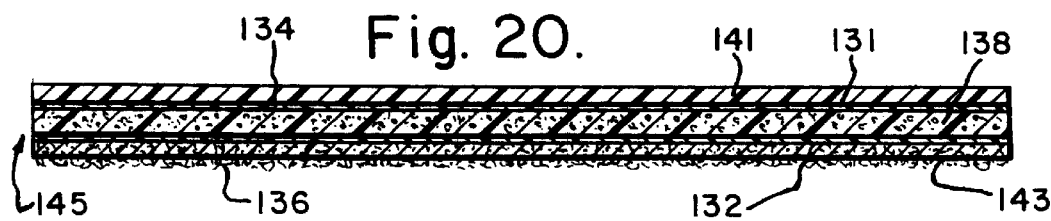
FIG. 20 is a view in section of a further embodiment of a shoe insert including a resilient layer.

FIG. 20 illustrates the use of pressure sensitive adhesive transfer tapes to manufacture the pad-receiving base for the shoe insert. Transfer tapes are marketed in the form of a thin strip of pressure-sensitive adhesive preapplied to a release liner and wound into a spiral on a hub. The transfer tapes are preferred over liquid adhesives, hot melt adhesives, staples, waxes or thermal or flame bonding. Heat may distort the cushioning layer or the HDPE base.

As the strip of adhesive is released from the liner it is sticky on both surfaces. It is readily automated to be used in continuous manufacturing operations. It is easy to quickly apply a neat precise strip of clean, dry adhesive strips 131, 132 such as 3MF-927 transfer tape to both sides 134, 136 of cushioning layer 138 such as a 62 mil thick layer of Poron resilient material.

By feeding the adhesive coated cushioning layer 138, a 20 mil thick film of polyethylene 141 and a continuous strip 143 of Veltex Bright loop cloth, a laminate 145 having the cross-section of FIG. 20 is formed. The shoe insert bases are then die cut from the laminate.

As an alternative, the loop fabric layer can be flame bonded to the cushioning material as a first operation. The fabric covered cushion layer can be adhesively bonded to the HDPE plastic base by means of adhesive transfer strips. Another alternative is to apply a second layer of loop cloth or loop cloth-cushion laminate to the other surface of the base.

Figure 21:
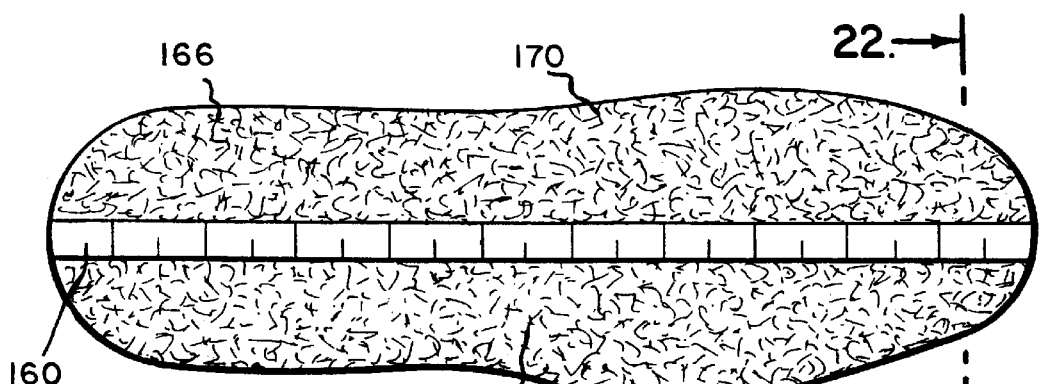
FIG. 21 is a view in elevation of a still further embodiment of a shoe insert containing a location guide.
Figure 22:
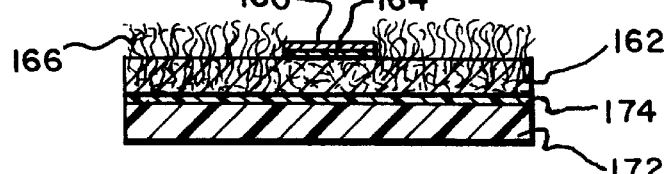
FIG. 22 is a view in section taken along line 22—22 of FIG. 21.

FIGS. 21–22 illustrates another embodiment of the invention. The pads must be precisely located. If they intrude under an inflamed area, it is very painful. To aid the user in locating the position, a visual index scale 160 can be bonded to the cushioning layer 162 by a film of adhesive 164 or to the cloth layer 166. When the scale 160 is bonded to the cushioning layer the cloth layer can be divided into 2 segments 168, 170 on each side of the scale 160. The scale could also be printed or silk-screened directly onto the cloth layer 166. A film 172 of deformable plastic is bonded by a film 174 of transfer tape or other adhesive means to the other surface of the cushioning layer 162.

Figure 23:
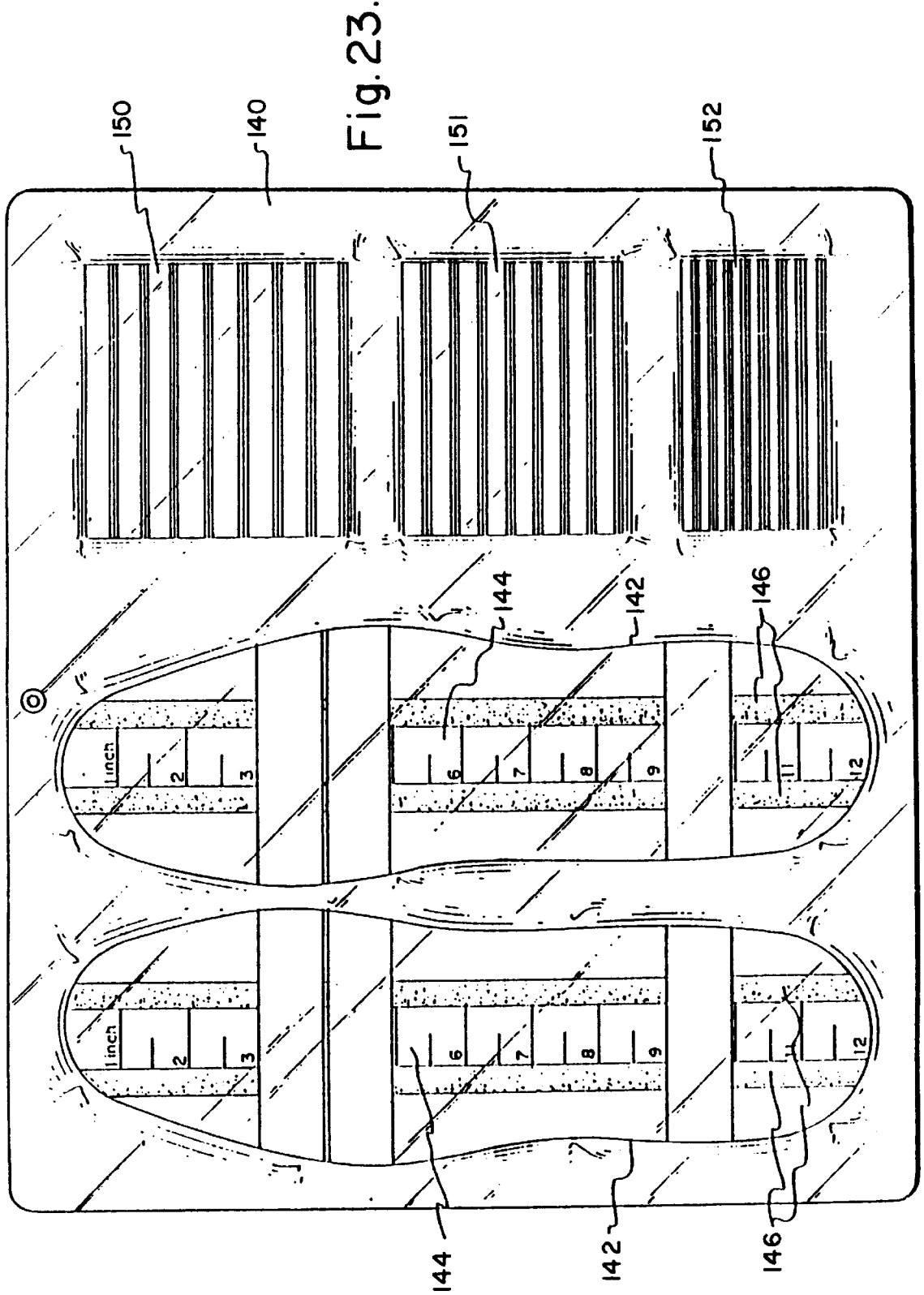
FIG. 23 is a plan view showing a kit of a shoe insert and cushion pad elements of varying thicknesses.

The use of strips of hook or loop material instead of a continuous layer is illustrated in FIG. 23.

A good way to deliver the insert to the user is shown in FIG. 23. A blister package 140 includes a pair of low friction insert 142, each having an index scale 144 thereon, with flanking strips 146 of adhesive or Velcro type fastening material. The user may use the scale to establish and maintain the discrete and movable cushion elements at the best locations that he discover with use. Normally the insert would be supplied fully covered with elements, but only three per insert are shown in FIG. 23 to help make the scale visible. Three groups of replacement cushion elements 150, 151, and 152 are also included that have a variety of thicknesses to help custom shape the insert. Even if the users foot shape requirements change with time, the kit of FIG. 23 allows continuing modification of the insert to an optimal configuration.

Sometimes the pads bind to the innersole of footwear during insertion into a shoe. The bottom layer can have a smooth low friction surface such as a thin vinyl or HDPE film. The assembly smoothly slides into the shoe. The bottom layer and/or top layer of the orthotic can include a layer which tricks moisture away from the foot such as polypropylene cloth or synthetic suede.

It is to be realized that only preferred embodiments of the invention have been described and that numerous substitutions, modifications and alterations are permissible without departing from the spirit and scope of the invention as defined in the following claims.

What is claimed is:

1. A shoe insert for placement on an inside surface of a shoe comprising in combination:

a shoe insole formed of non-compressible sheet of deformable synthetic organic thermoplastic resin having a thickness of up to 50 mils and being shaped to fit over said inside surface of a shoe, said sheet having memory to permanently retain a deformed shape and said sheet having a continuous, smooth, seamless upper surface and having a bottom surface; and the bottom surface of said sheet including a layer of first fastening material selected from loop fabric or hook fabric and a plurality of cushion pad elements, each containing a layer of resilient compressible, cushioning material and each having a top surface including a layer of second fastening material releasably engageable with said first fastening material selected from loop fabric or hook fabric, said elements being attached to said layer of first fastening material and at least one of said elements containing a thicker layer of cushioning material whereby when the insert is placed on the inside surface of a shoe, said elements compress under the weight of the user, the sheet deforms in the space between the elements and at locations where adjacent pad elements differ in thickness and retains a deformed shape when the force from the user's weight is removed to selectively modify the elevation or pitch of said insert relative to said inside surface of said shoe.

2. A shoe insert according to claim 1 in which said upper surface is smooth and continuous.

3. A shoe insert according to claim 1 in which at least one of said cushion pad elements has a thickness differing from other of said elements.

4. A shoe insert according to claim 1 in which the fastening material attached to the bottom surface of said deformable sheet comprises a loop fabric, and the fastening material attached to the top surface of said cushioning material comprises a hook fabric.

5. A shoe insert according to claim 1 in which
   said first fastening means is attached to a sufficient portion of said bottom surface to allow said cushion pad elements to be placed anywhere on said bottom surface.

6. A shoe insert according to claim 1 in which said sheet further comprises a layer of a high density polyethylene.

* * * * *